US00PP12108P2

(12) United States Plant Patent
Deroose

(10) Patent No.: US PP12,108 P2
(45) Date of Patent: Oct. 2, 2001

(54) GUZMANIA PLANT NAMED 'MARINA'

(75) Inventor: Reginald Deroose, Evergem (BE)

(73) Assignee: Deroose Plants BVBA, Evergem (BE)

( * ) Notice: Subject to any disclaimer, the term of this patent is extended or adjusted under 35 U.S.C. 154(b) by 0 days.

(21) Appl. No.: 09/401,846

(22) Filed: Sep. 22, 1999

(51) Int. Cl.[7] ..... A01H 5/00
(52) U.S. Cl. ..... Plt./371
(58) Field of Search ..... Plt./371

(56) References Cited

U.S. PATENT DOCUMENTS

P.P. 9,476 * 3/1996 Kent ..... Plt./371
P.P. 10,069 * 10/1997 Kent ..... Plt./371
P.P. 10,383 * 5/1998 Bos ..... Plt./371

OTHER PUBLICATIONS

GTITM UPOVROM Citation for 'Marina' as Per QZ PBR 991030; Jul. 19, 1999.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A Guzmania plant named 'Marina' characterized by having a vigorous growth habit, variegated foliage that is slightly red at the sheath becoming cream-white at the apex of the leaf, and compact, red-colored inflorescence with yellow flowers.

1 Drawing Sheet

BACKGROUND OF THE INVENTION

The present invention comprises a new and distinct cultivar of Guzmania plant, hereinafter referred to by the cultivar name 'Marina'. The genus Guzmania is a member of the family Bromeliaceae.

Guzmania is predominantly epiphytic with a few terrestrial species and is native to the tropics. For the most part, species vary in diameter from 7 or 8 inches to 3 or 4 feet and have rosettes of glossy, smooth-edged leaves.

Floral bracts of Guzmania frequently have brilliant colors and may last for many months. The range of colors for Guzmania is generally from yellow through orange but may also include flame red and red-purple. White or yellow, tubular, three-petalled flowers may also appear on a stem or within the leaf rosette but are usually short-lived.

Guzmania may be advantageously grown as pot plants for greenhouse or home use. Desirably, the plants are shaded from direct sunlight, and during the spring to autumn period, the central vase-like part of the leaf rosette is desirably filled with water.

Guzmania is native to tropical America. Leaves of Guzmania are usually formed as basal rosettes, which are stiff and entire and in several vertical ranks. Guzmania plants have terminal spikes or panicles which are often bracted with petals united in a tube about as long as the calyx. The ovary is superior and the seeds plumose.

Asexual propagation of Guzmania is frequently done through the use of tissue culture practices. Propagation can also be from offshoots produced by the plant which may then be rooted. The resulting plantlets are detached from the mother plant and may be potted in a suitable growing mixture.

Methods for cultivation and crossing of Guzmania are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, *BROMELIEN*, Verlag Paul Parey, Berlin (1986); and Rauh, Werner, *BROMELIEN*, Verlag Eugen Ulmer, Stuttgart (1981).

The new cultivar was discovered as a naturally occurring mutation among plants of the parent cultivar 'Muriel' (unpatented), which is a non-variegated Guzmania plant. 'Marina' was discovered and selected by the inventor, Reginald Deroose, in 1990, in a controlled environment in Evergem, Belgium.

'Marina' is characterized by its medium to large plant size, vigorous growth habit and variegated leaves that are slightly red at the sheath becoming cream-white at the apex. The inflorescence is compact and red-colored.

The first act of asexual reproduction of the new cultivar was performed by the inventor, in 1990, from offshoots produced by the plant. Horticultural examination of these asexually reproduced plants initiated in 1990 has demonstrated that the combination of characteristics as herein disclosed for 'Marina' are firmly fixed and reproduces true to type through successive generations of asexual reproduction.

BRIEF DESCRIPTION OF THE INVENTION

The following traits have been repeatedly observed and are determined to be basic characteristics of 'Marina' which in combination distinguish this Guzmania as a new and distinct cultivar:

1. Vigorous growth habit;

2. Variegated foliage that is slightly red at the sheath becoming cream-white at the apex of the leaf; and 3. Compact, red-colored inflorescence with yellow flowers.

'Marina' has not been observed under all possible environmental conditions. The phenotype of the new cultivar may vary significantly with variations in environment such as temperature, light intensity, and daylength, without any change in genotype.

Of the many commercial cultivars known to the present inventor, the most similar in comparison to 'Marina' is the parental cultivar 'Muriel'. The plant shape and inflorescence of 'Marina' are similar to those of 'Muriel'. The leaves of 'Marina' are variegated while the leaves of 'Muriel' are green thoughout.

BRIEF DESCRIPTION OF THE DRAWING

The accompanying photographic illustration shows a perspective view of the inflorescence and foliage characteristics of a typical 'Marina' plant, with colors being as true as possible with illustrations of this type.

DETAILED BOTANICAL DESCRIPTION

The following observations, measurements and values describe plants grown in Evergem, Belgium, under greenhouse conditions which closely approximate those generally used in horticultural practice. The plant described is approximately 13 months old from a 25 cm long cutting, for a plant height of 50 cm (including 10 cm pot). Color references are made to The Royal Horticultural Society Colour Chart (R.H.S.), except where general colors of ordinary significance are used.

Classification: Commercial: Guzmania c.v. 'Marina'.

Species: Guzmania 'Marina' is a variegated mutant of Guzmania 'Muriel'. Guzmania 'Muriel' is Guzmania 'Magnifica'×*Guzmania zahnii*. Guzmania 'Magnifica' is *Guzmania lingulata* v. *cardinalis*×*Guzmania lingulata* v. *minor*.

Parentage: Naturally occurring mutation of Guzmania 'Muriel'.

Propagation: Vegetative, by removal of offsets.

Plant:

*Form.*—Funnel-form rosette.

*Height.*—Approximately 48–50 cm when flowering.

*Diameter.*—Approximately 70–75 cm.

*Growth habit.*—Vigorous, it takes approximately 13 months to produce a finished flowering plant from a 25 cm long cutting, in a standard heated greenhouse with temperatures during the day of 20 degrees Celsius, and 18 degrees Celsius at night.

Foliage:

*Habit.*—Arcuate spreading, leaves are upstanding at an angle of 45° and bend downward from the middle.

*Size.*—Approximately 40–50 cm long.

*Leaf sheaths.*—Elliptic, 5 cm wide; margins are green (RHS 146A) with red striations (RHS 59B); middle is cream-white (RHS 158B) with green (RHS 146A) and red (RHS 59B) striations (color designations are for both upper and lower surfaces).

*Leaf blades.*—Ligulate, apex is acute to attenuate, 3 cm wide, variegated ⅓ to ½ of the surface. The variegation is pointed toward the apex of the leaf blade and shows irregularly green striations. The margins are green (RHS 147A). The central zone of the leaf is cream-white (RHS 157B) with irregularly green (RHS 147A) striations (color designations are for both upper and lower surfaces), margin is entire.

*Scape.*—Approximately 48–50 cm long and 1 cm in diameter.

*Scape bracts.*—Approximately 12, imbricate, foliaceous, concealing the scape, slightly arcuate spreading, up to 14 cm long and 2 cm wide, variegation similar to the leaves. There is a gradual transition from leaves to scape bracts from the bottom to the top with a red-colored (RHS 51B and RHS 46A , for both upper and lower surfaces) appearance of the bracts; margin is entire; apex is acute to attenuate.

*Number of leaves.*—30 to 35.

Inflorescence:

*Habit.*—Spike, round, 12–15 cm in diameter, the part where the primary bracts are positioned is rather compressed with approximately 20 spirally arranged bracts that bend at an angle of 90°.

*Length/width.*—5 cm long, 5 cm wide.

*Primary bracts.*—Approximately 18, elliptic in shape, apex is acute to attenuate, margin is entire, 2.5–6 cm long and 1–2.5 cm wide, red (RHS 46A for both upper and lower surfaces).

*Floral bracts.*—1 floral bract per flower, entire shape is elliptic; apex is cucullate; base is sessile; margin is entire, approximately 1 cm wide; 25–30 mm long, red (RHS 46A, for both upper and lower surfaces).

*Flowers.*—Diameter/length: 5 mm diameter, 2 cm long. Habit: One flower per floral bract, many flowering at the same time, 15–25 flowers per primary bract, 250–450 flowers per plant. Sepals: 3, white in color (RHS 155C) with a touch of red (RHS 51B) towards the cucullate apex, entire shape is elliptic, approximately 2 cm long, 4–5 cm wide, base is sessile, margin is entire (Color designations represent both upper and lower surfaces). Petals: 3, yellow in color (RHS 15C) (both surfaces) and tubular in shape at the bottom, entire shape is elliptic, approximately 1.5 cm long, 3–4 cm wide, apex is cucullate, base is sessile, margin is entire. Stamens: White, 2.5 cm long, 6 per flower, lower parts of filaments fused with the petals. Pistils: 2 to 2.2 cm long, 1 per flower with a 3 lobed style.

*Duration of flowers.*—Individual flowers last for one day and the total duration of flowering is approximately 12 weeks.

*Buds.*—Entire shape elliptic, approximately 2.5 cm long, 3 mm diameter, white in color.

Other significant characteristics: The inflorescence holds its color for 5 to 7 months.

Pollen: No known pollen produced.

Fruit: No fruit produced.

Disease/pest resistance/susceptibility: No specific resistance or susceptibility observed.

I claim:

1. A new and distinct Guzmania plant named 'Marina', substantially as illustrated and described herein.

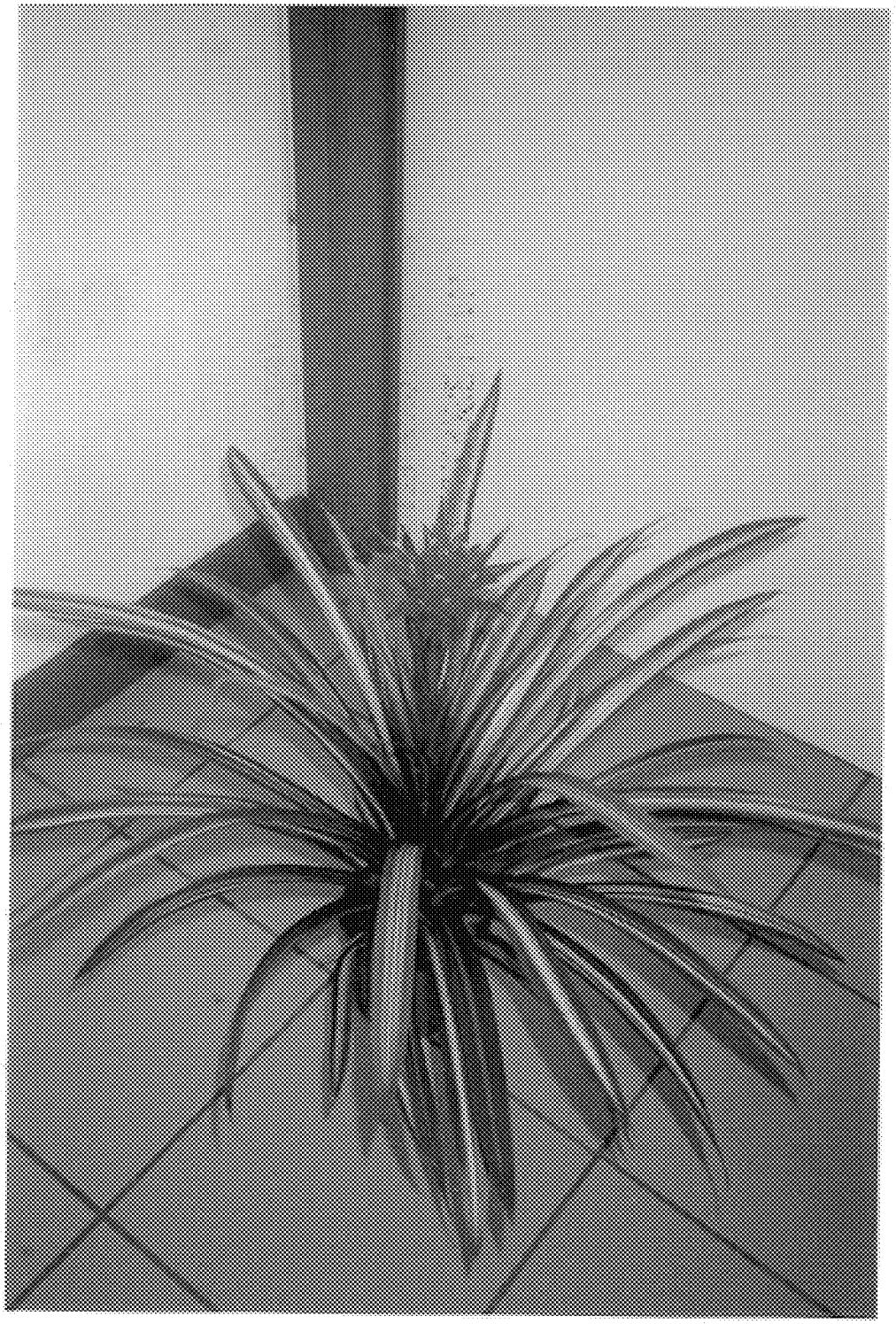

* * * * *